United States Patent
Reddy et al.

(10) Patent No.: US 11,222,720 B2
(45) Date of Patent: *Jan. 11, 2022

(54) METHOD FOR TRACKING CONSUMPTION OF SUPPLEMENTS BY A USER

(71) Applicant: Serotonin, Inc., San Francisco, CA (US)

(72) Inventors: Rajesh Reddy, San Francisco, CA (US); Matt Leanse, San Francisco, CA (US); Julian Philips, San Francisco, CA (US); Amoghavarsha Janakaloti Shamarao, Bengaluru (IN)

(73) Assignee: Serotonin, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/993,025

(22) Filed: Aug. 13, 2020

(65) Prior Publication Data

US 2020/0373000 A1 Nov. 26, 2020

Related U.S. Application Data

(63) Continuation of application No. 16/052,187, filed on Aug. 1, 2018, now Pat. No. 10,777,316.

(Continued)

(51) Int. Cl.
*G06F 17/00* (2019.01)
*G06K 19/06* (2006.01)
(Continued)

(52) U.S. Cl.
CPC ......... *G16H 20/60* (2018.01); *G06Q 30/0282* (2013.01); *G08B 21/24* (2013.01);
(Continued)

(58) Field of Classification Search
CPC ........ G16H 20/60; G16H 20/13; G16H 40/63; H04M 1/72412; G06Q 30/0282; G06Q 50/01; G09B 19/0092; G08B 21/24
See application file for complete search history.

(56) References Cited

U.S. PATENT DOCUMENTS

2008/0030309 A1\* 2/2008 Darrouzet .............. G16H 20/13
340/309.7
2008/0210701 A1\* 9/2008 Cooper ................ A61J 7/0481
221/3

(Continued)

*Primary Examiner* — Tuyen K Vo
(74) *Attorney, Agent, or Firm* — Run8 Patent Group, LLC; Peter Miller

(57) ABSTRACT

One variation of a method for tracking consumption of supplements by a user includes, at a software program executing on a mobile computing device: receiving a selection of a supplement, from a set of known supplements, contained in a supplement package of a particular packaging format; loading a supplement profile of the supplement into a user profile; rendering an instruction for placement of a tracker on the supplement based on the packaging format; retrieving a motion model, from a set of motion models for characterizing a consumption event at the packaging format; and uploading the motion model to the tracker. The method also includes, at the tracker: characterizing motion of the supplement package as a consumption event based on the motion model; and transmitting a time of the consumption event to the mobile computing device.

19 Claims, 3 Drawing Sheets

Related U.S. Application Data

(60) Provisional application No. 62/547,741, filed on Aug. 18, 2017, provisional application No. 62/547,738, filed on Aug. 18, 2017, provisional application No. 62/547,744, filed on Aug. 18, 2017.

(51) Int. Cl.
| | |
|---|---|
| *G16H 20/60* | (2018.01) |
| *G09B 19/00* | (2006.01) |
| *G08B 21/24* | (2006.01) |
| *H04M 1/72412* | (2021.01) |
| *G06Q 30/02* | (2012.01) |
| *G06Q 50/00* | (2012.01) |

(52) U.S. Cl.
CPC .... *G09B 19/0092* (2013.01); *H04M 1/72412* (2021.01); *G06Q 50/01* (2013.01)

(56) References Cited

U.S. PATENT DOCUMENTS

| | | | |
|---|---|---|---|
| 2012/0179665 A1* | 7/2012 | Baarman | G16H 20/60 707/709 |
| 2015/0058041 A1* | 2/2015 | Ervin | G16H 10/60 705/3 |
| 2016/0327427 A1* | 11/2016 | Briones | A61J 7/0436 |
| 2020/0152312 A1* | 5/2020 | Connor | G06K 9/00335 |

\* cited by examiner

METHOD FOR TRACKING CONSUMPTION OF SUPPLEMENTS BY A USER

CROSS-REFERENCE TO RELATED APPLICATIONS

This Application is a continuation application of U.S. patent application Ser. No. 16/052,187, filed on 1 Aug. 2018, which claims the benefit of U.S. Provisional Application Nos. 62/547,738, 62/547,741, and 62/547,744, all filed on 18 Aug. 2017, each of which is incorporated in its entirety by this reference.

TECHNICAL FIELD

This invention relates generally to the field of health and wellness and more specifically to a new and useful method for tracking consumption of supplements by a user in the field of health and wellness.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
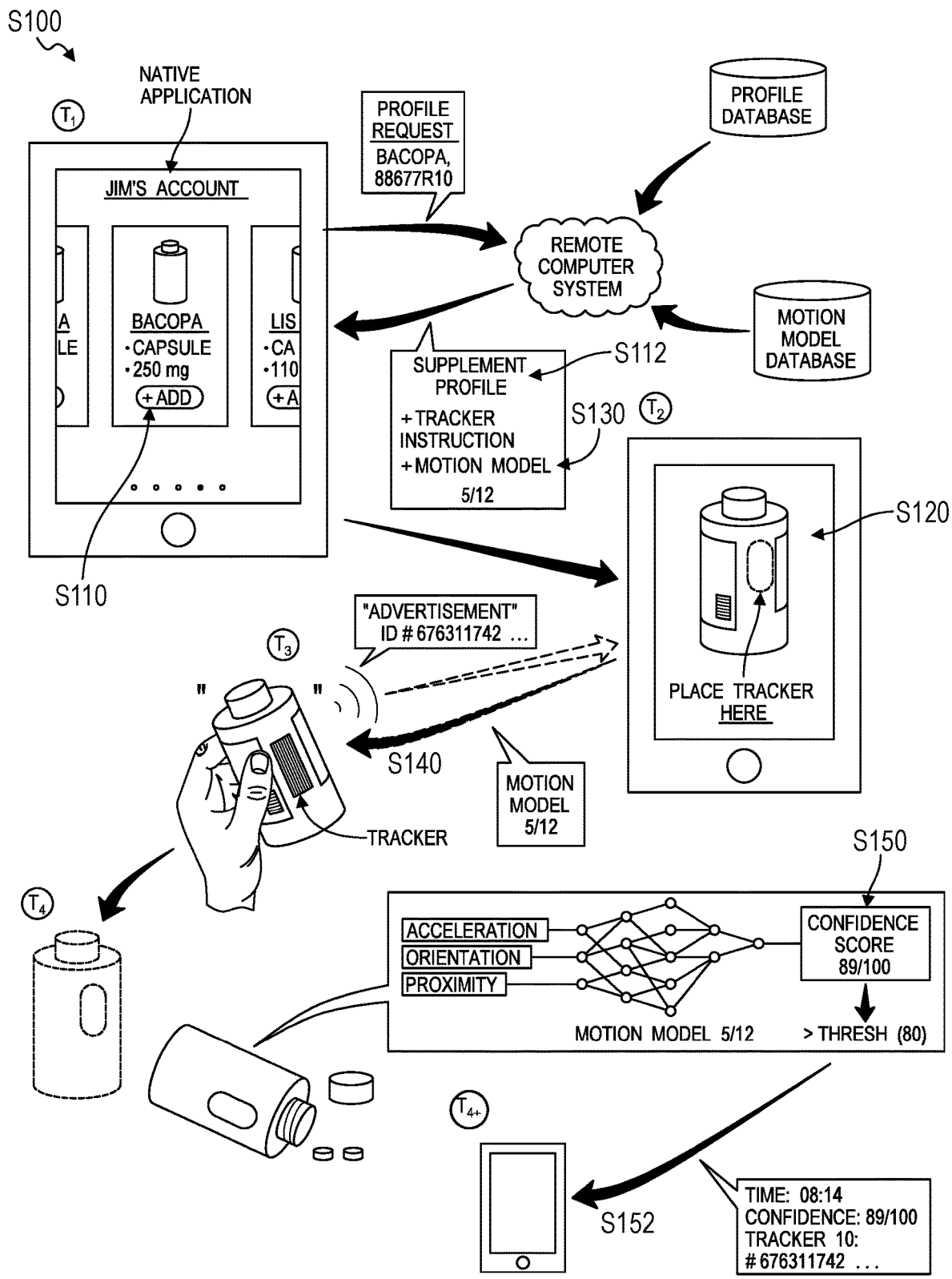
FIG. 1 is a flowchart representation of a first method.

As shown in FIG. 1, a first method S100 for tracking consumption of supplements by a user includes, at a software program executing on a mobile computing device: receiving a selection of a supplement, from a set of known supplements, contained in a supplement package of a particular packaging format in Block S110; loading a supplement profile of the supplement into a user account in Block S112; rendering an instruction for placement of a tracker on the supplement based on the packaging format in Block S120; retrieving a motion model, from a set of motion models for characterizing a consumption event at the packaging format in Block S130; and uploading the motion model to the tracker in Block S140. The first method S100 also includes, at the tracker: characterizing motion of the supplement package as a consumption event based on the motion model in Block S150; and transmitting a time of the consumption event to the mobile computing device in Block S152.

1.1 Applications

The first method S100 can be executed by a system including a wireless tracker and a software program (hereinafter a "native application" executing on a mobile computing device) to track consumption of a variety of supplements of different types by a user over time. In particular, the native application hosts a user account on a user's mobile computing device (e.g., smartphone, tablet, smartwatch), enables the user to add and remove supplements from her user account, enables the user to set and adjust a regimen for consumption of these supplements, serves notifications to the user to consume these supplements according to regimens defined by the user, and interfaces with a set of like trackers (e.g., identical trackers) to track consumption of supplement doses by the user from a set of supplement packages. When a new supplement is added to the user account or the user receives a new supplement package filled with a supplement already in the user account, the native application also automatically configures the tracker to detect dosing events at this supplement package by: accessing a supplement package type of the supplement package, such as from an optical scan of the software program package performed by the user with the mobile computing device or based on the supplement profile in the user's account; instructing the user where to place the tracker on the supplement package based on the supplement package type; and then uploading a motion model—from a set of motion models for various supplement package types—configured to detect consumption events at supplement packages of the supplement package type to the supplement package. By then collecting motion and/or other data over time and passing these data into the motion model, the tracker can detect consumption events, that is, instances in which the user removes one or more doses from the supplement package.

Generally, supplements may be packaged (and repackaged) in various packaging formats, such as large jars, small jars, dropper bottles, packets, bags, boxes, etc. Similarly, supplements may be consumed in various formats, such as capsule form, powder, liquid, teabag, etc. Each unique combination of packaging format and supplement format can yield a unique motion signature at the supplement package during a dosing event. For example, a five-liter jar containing supplement in powder format may be manipulated by a user during a dosing event in a way very different from how a user manipulates a three-ounce bottle containing liquid supplement dispensed from a dropper during a dosing event. Therefore, when a tracker is mounted to a supplement package, the native application can: retrieve a motion model (e.g., a recurrent neural network) specifically configured to detect a dosing event for the combination of packaging format and supplement format for this supplement package; and upload this motion model to the tracker for local detection of dosing events. When the tracker is later moved to a different supplement package, such as of a different packaging format and/or containing supplements in a different supplement format, once the previous supplement package is emptied or when the user decides to transition to a different supplement, the native application can repeat this process to: retrieve another motion model specific to this new packaging format and/or supplement format; and upload this other motion model to the tracker.

The tracker can be powered by a battery configured to track its motion, characterize its motion as a consumption event based on a motion model loaded into its memory, and to transmit timestamps and other metadata of such consumption events to the mobile computing device for recording by the native application over an extended period of time, such as one year. Because supplements may have limited shelf lives (e.g., weeks or months): the tracker may be moved from one supplement package to another over time, such as between supplement packages of the same or different packaging format and containing supplements in the same or different supplement format; and the native application can automatically update the motion model on the tracker when mounted to a new supplement package once a packaging format and supplement format in the new supplement package are known.

Therefore, rather than interface with "smart" bottles, "smart" bottle caps, and other tracking systems of many (e.g., hundreds) of packaging types to accommodate the wide range of packaging formats in which supplements are supplied, the native application can: interface with a single type of tracker configured to transiently (i.e., non-permanently) mount to many packaging types; and reconfigure each instance of the tracker in software to accommodate the combination of packaging format and supplement format that the instance of the tracker is installed on. Furthermore, a single instance of this common tracker can be installed on multiple supplement packages over time as these supplement packages are emptied and/or as the user transitions to other supplements, thereby amortizing the cost of the instance of the tracker over multiple supplement packages while also requiring no change or standardization of packing types and requiring minimal effort on the part of a user to manage and maintain a fleet of trackers to track her consumption of multiple supplements over time. The native application can then receive timestamps and/or other metadata of consumption events from these trackers to monitor the user's adherence to corresponding regimens and selectively serve notifications to consume these supplements over time based on these regimens, the user's historical consumption data, and proximity of the mobile computing device to these trackers.

1.2 Tracker

Generally, the tracker is configured to transiently install on a supplement package, to detect consumption events, and to wirelessly transmit consumption event data to a mobile computing device executing an instance of the native application for logging of consumption events in a user account hosted on the native application.

Figure 2:
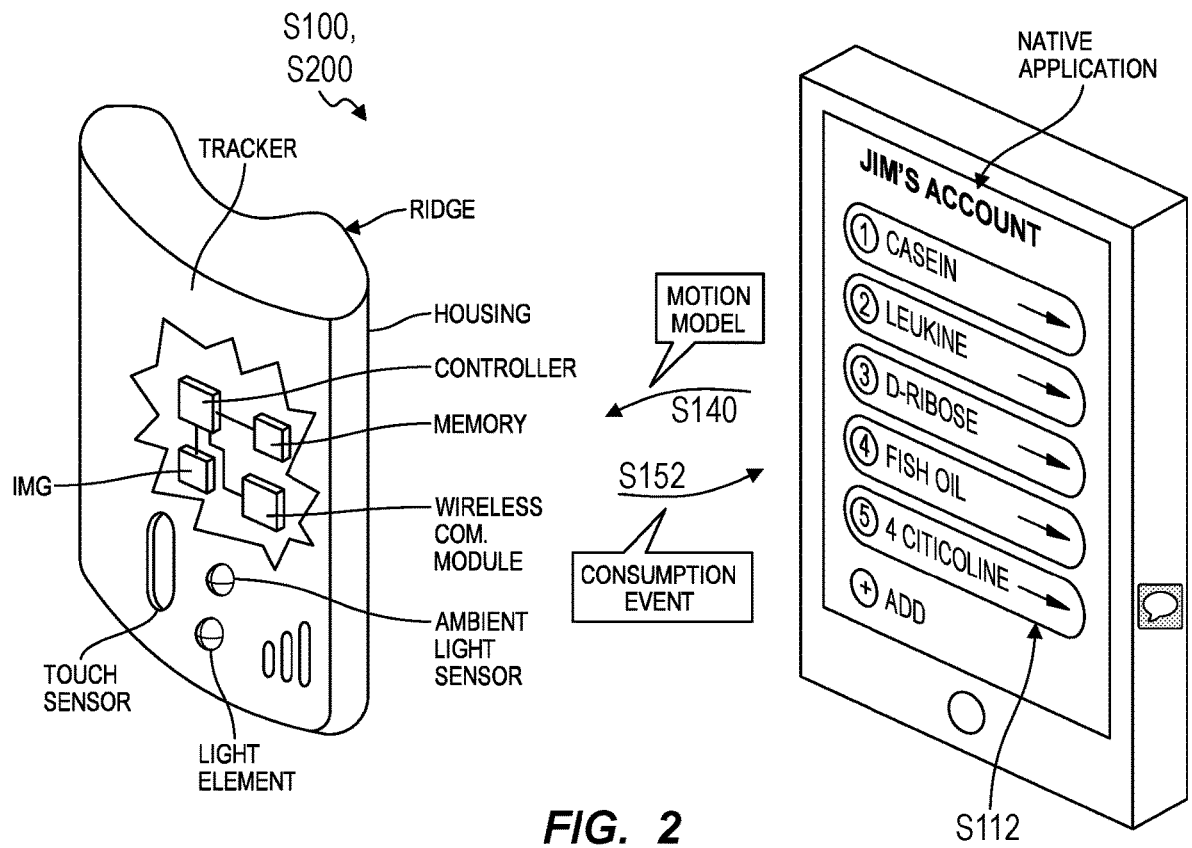
FIG. 2 is a flowchart representation of one variation of the first method.

In one implementation shown in FIG. 2, the tracker includes: a housing; a memory module arranged in the housing and configured to store motion data in a buffer and to store a motion model received from the native application; a touch and/or proximity sensor (e.g., a capacitance sensor) arranged in the housing and configured to detect a body (e.g., that is conductive or exhibits a dielectric different from air) in contact with or near the housing; and ambient light sensor arranged in the housing and configured to detect a change in ambient light around the housing; a motion sensor (e.g., an accelerometer, a gyroscope, a tilt sensor, an IMU) arranged in the housing and configured to output a signal corresponding to movement of the housing; a controller configured to collect data from the touch sensor, the ambient light sensor, and/or the motion sensor and to pass these data through a motion model stored locally in the memory module to identify a consumption event; a feedback element, such as in the form of a light element (e.g., an LED) and/or haptic module (e.g., a vibrator), arranged in the housing and configured to output a signal indicating a state of the controller; a wireless communication module configured to transmit consumption event data to an affiliated mobile computing device; and a battery configured to power the foregoing modules, such as over a period of several months or years.

Figure 3:
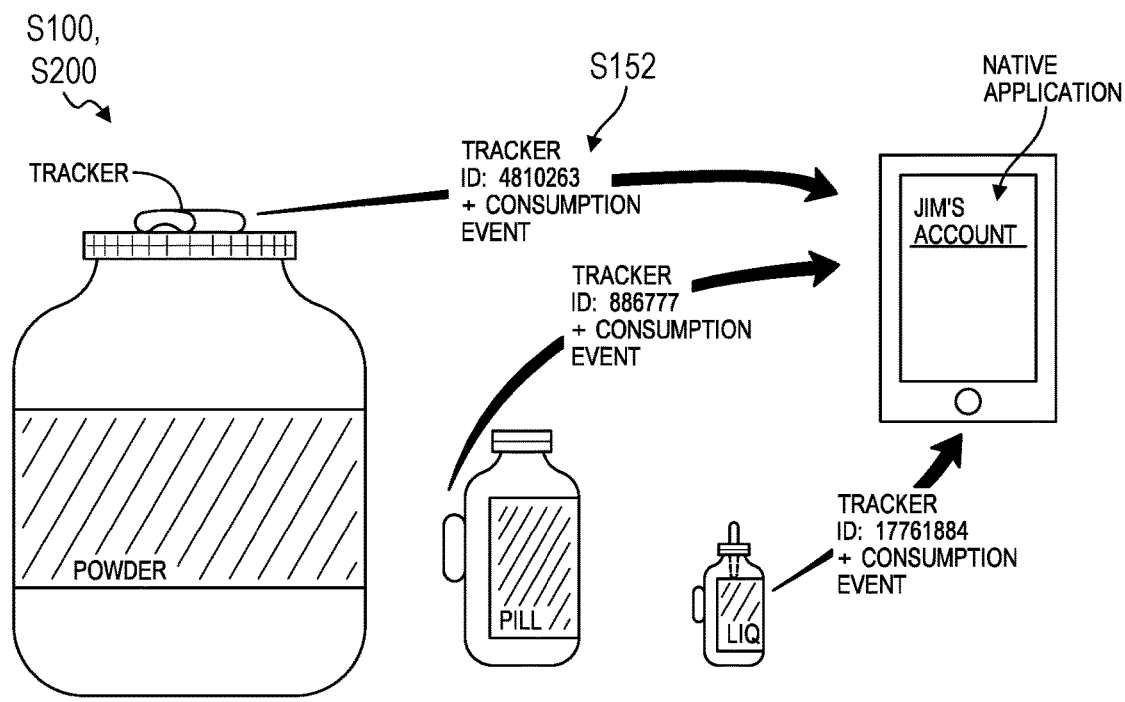
FIG. 3 is a flowchart representation of one variation of the first method.

In this implementation, the housing can define: an inner surface configured to face a supplement package; and an outer surface opposite the inwardly facing surface. The housing can also define two laterally-offset ridges extending vertically along the inner surface of the housing and configured to mate with supplement packages of various sizes and geometries (e.g., round bottles and jars, flat lid tops, etc.), as shown in FIGS. 2 and 3. Such geometry of the housing can limit installation of the tracker on a side of a supplement package to one of an upright vertical orientation or an inverted vertical orientation to achieve sufficient mating between the inner surface of the housing and the supplement package, thereby enabling the controller to predict an orientation of the housing on a supplement package to a relatively high degree of confidence.

A transient attachment interface can also be coupled to the inner surface of the housing, such as extending along each of the two ridges, thereby enabling the tracker to be removed from one supplement package and installed on another supplement package over time. For example, one element of a two-part hook-and-loop attachment system can be (permanently) adhered to the inner surface of the housing; a second element of the two-part hook-and-loop attachment system can be manually applied to a side of a supplement package; and the tracker can then be placed over the second element to transiently couple the tracker to the supplement package. When the supplement package is empty, the supplement package can be discarded with the second element. Another instance of the second element can be manually installed on a second supplement package, and the tracker can be placed over the second instance of the second element to transiently couple the tracker to the second supplement package. Alternatively, the tracker can be installed with double-sided tape, an elastic band, a suction cup, or any other transient attachment system.

The light element can include an LED arranged on the inner face of the housing and configured to illuminate a translucent supplement package (e.g., an amber glass bottle) physically paired with the tracker. The tracker can additionally or alternatively include a light element arranged on the outer face of the housing.

However, the tracker can include any other elements, can define any other geometry, and can be transiently mounted to a supplement package in any other way.

1.3 Software Program

As shown in FIGS. 1 and 2, the software program defines a native application configured; to execute on a mobile computing device (e.g., a smartphone, a tablet, and smartwatch); to host a portal into an electronic user account; to manage supplement profiles loaded into the user account by a user; to automatically reconfigure trackers installed on supplement packages when corresponding supplements are added to or updated in the user account; to receive consumption event data from these trackers; to load consumption events; and to selectively serve notifications to the user to consume supplements according to regimens associated with these supplements in the user account.

Additionally or alternatively, the software program can be implemented in a web browser, such as on the user's mobile computing device or at a desktop computer.

1.4 Manual Loading of Supplement Profile into User Account

Block S110 of the first method S100 recites, at a software program (hereinafter the "native application") executing on a mobile computing device, receiving a selection of a supplement, from a set of known supplements, contained in a supplement package of a particular packaging format; and Block S112 of the first method S100 recites loading a supplement profile of the supplement into a user account. Generally, in Blocks S110 and S112, the native application adds a supplement to the user's account, such as to a virtual "shelf" in the user's account, based on an input received from the user.

In one implementation, to load a new supplement to the user account, the user records a photographic image or a camera feed (i.e., a "scan") of a barcode or other label on the supplement package. The native application accesses this image or a camera feed, implements computer vision techniques to extract an identifier (e.g., a SKU) of the supplement package from this image or camera feed, retrieves a supplement profile associated with this identifier from a remote database, and then loads the supplement profile into the user's account. For example, the supplement profile can specify: a name of the supplement; a format of the supplement (e.g., capsule form, powder, etc.); a size of one dose of the supplement (e.g., 100 milligrams per pill, 30 grams per scoop, etc.); a packaging format and size of the supplement packaging (e.g., three-ounce amber glass bottle with dropper lid, eight-ounce white plastic jar with pop lid, five-liter white plastic jar with screw lid); ingredients; a consumption recommendation or regimen (e.g., recommended or maximum doses per day); etc.

In another implementation, the user can manually enter search terms for a new supplement into the native application—such as a name, size, or SKU of the supplement or supplement package—and the native application can retrieve a supplement profile of a supplement selected from results of the user's search, as shown in FIG. 1.

In yet another implementation, the native application can interface with a social network to enable the user to view supplements loaded into profiles of other users, such as friends, family, and other acquaintances of the user. The user can thus select a supplement shown in another user's account to copy the supplement into the user's own profile; the native application can thus retrieve a corresponding supplement profile and load the supplement profile into the user's account, as described above.

1.5 Tracker Pairing

Once a supplement profile is thus added to the user's account, the user can confirm whether consumption of supplements from the supplement package is to be monitored with a tracker. For example, the user can manually toggle a virtual switch in the supplement profile or adjacent an image of the supplement or supplement package in a virtual shelf in the user's account rendered in the native application. If the user indicates that the consumption of the supplement is to be monitored with a tracker coupled to the supplement package, the native application can interface with the tracker to execute a paring routine to link a tracker to the user account and to confirm a physical connection between the tracker and the supplement package.

1.5.1 Guidance

Block S120 of the first method S100 recites, in response to receipt of a wireless query from a tracker, rendering an instruction for placement of the tracker on the supplement based on the packaging format. Generally, in Block S120, the native application can serve textual and/or visual guidance to a user for placement of a tracker on the supplement package, as shown in FIG. 1. In particular, motion models for characterizing motion (and/or other sensor streams) of a tracker as a consumption event may be trained on specific combinations of supplement format and packaging format. To ensure that a motion model uploaded to the tracker in Block S140 is capable of characterizing motion of the tracker with a high degree of accuracy (i.e., low false positive rate and a low false negative rate), the native application can provide specific instructions for installing the tracker on the supplement package to the user. For example, each motion model can include a recurrent neural network trained on motion data—collected previously from trackers coupled to supplement packages of similar packaging format containing supplements of similar supplement format—labeled as representing and/or not representing consumption events, such as by other users or technicians. To provide a greatest likelihood that a motion model—for a particular combination of packaging format and supplement format for a new supplement added to the user's account—will detect a consumption event at the supplement package, the native application can explicitly instruct the user to place a tracker at a location on the supplement package that aligns with placement of these other trackers on these other like supplement packages.

In one implementation, when retrieving the supplement profile from the database of supplement profiles, the native application also retrieves a graphic (e.g., a cartoon) or animation depicting a target location of the tracker on the supplement package, as shown in FIG. 1. In particular, the supplement profile of the supplement can specify a format of the supplement and a packaging format of the supplement package, including a type and size of the supplement package, as described above. The native application can then query a remote database for a tracker placement graphic for this combination of supplement format and packaging format and render this graphic on a display of the mobile computing device; the user can then place a tracker on the supplement package as instructed by this tracker placement graphic.

For example, for a large white (i.e., opaque) supplement package containing supplement in powdered form, the tracker placement graphic can depict placement of the tracker on a lid of the supplement package. In another example, for a small white supplement package containing supplement in capsule form, the tracker placement graphic can depict placement of the tracker over a label on the supplement package adjacent a barcode. In yet another example, for a glass supplement package containing supplement in liquid form dispensed by a dropper, the tracker placement graphic can depict placement of the tracker just below a neck of the supplement package (e.g., when the proximity sensor may detect presence and removal of the dropper) over a region not obscured by a label (thereby enabling an inward-facing light element to illuminate the bottle). In another example, for a glass supplement package containing supplement in capsule form, the tracker placement graphic can depict placement of the tracker near a base of the supplement package over a region not obscured by a label.

Additionally or alternatively, the system can provide a textual description for target placement of the tracker on the supplement package or communicate such information in any other way.

1.5.2 Tracker Detection

Upon viewing instructions provided by the native application, the user may install the tracker on the supplement package accordingly. The user can then tap, double-tap, shake, or otherwise manipulate the tracker to prompt the tracker to pair with the mobile computing device. The tracker can monitor its motion through its integrated motion sensors and then broadcast an advertisement or query—including an identifier of the tracker (e.g., a universally unique identifier, or "UUID") and a request to connect to a local computing device—if its motion (e.g., acceleration) exceeds a predefined threshold, as shown in FIG. 1. Upon receipt of this query from the tracker, the native application can: establish a wireless connection to the tracker; and link the identifier of the tracker to the supplement profile in the user's account. For example, the user can tap the mobile computing device against the tracker; this impact can trigger the tracker to broadcast a query to connect to a computing device nearby; the native application can also register this impact through motion sensors in the mobile computing device and record this connection between the identifier of the tracker and the supplement profile based on receipt of this query from the tracker just after registering this impact. In this example, the native application can also confirm this impact between the mobile computing device and the tracker and thus confirm the connection between the identifier of the tracker and the supplement profile in Block S122 based on a high signal strength of the query received from the tracker (i.e., due to proximity between the tracker and the mobile computing device at the time of the impact).

In another implementation, the tracker wakes into an active mode automatically when outputs of various sensors in the tracker indicate that the tracker is being placed on a supplement package. For example, the tracker can wake and broadcast a query, as described above, when a set of environmental conditions are met, including: a change in output of the touch or proximity sensor (e.g., a capacitance sensor) indicating presence of a body (e.g., a hand) on or near the tracker; a drop in ambient light level detected by the ambient light sensor indicating that the ambient light sensor is obscured by a hand or finger; and acceleration followed by deceleration of the tracker indicates that the tracker is being placed on a supplement package. Upon receipt of the query—including the tracker identifier—from the tracker, the native application can link tracker identifier to the supplement profile in the user's account, as described above.

In the foregoing implementation, the tracker can be configured to execute this process during first use (i.e., "out of the box"). However, if the tracker has been previously used on another supplement package, the native application can predict that the particular tracker—such as in a set of trackers maintained by the user—will be moved to another supplement package if a supplement package previously linked to the tracker is determined to be empty or if the user removes a supplement profile previously linked to the tracker from her user account; the native application can then broadcast a command to the tracker to prepare for detection or transfer to another supplement package.

However, the tracker can initiate a wireless connection with the mobile computing device in any other way and in response to any other event to prompt the native application to link the tracker to a supplement profile—representative of the physical supplement package physically paired with the tracker—in the user's account.

1.5.3 Automatic Loading of Supplement Profile into User Account

In one variation, the user: initiates a paring routine at the native application, such as by adding a new supplement profile to her user account, as described above; removes a new tracker from its packaging or removes a used tracker from an empty, expired, or discarded supplement package; places the tracker on a supplement package, such as near a barcode (or other visual identifier); holds the supplement package—with tracker attached—in one hand while capturing a photographic image of the barcode with the mobile computing device held in her other hand. Upon receipt of this photographic image, the native application triggers the mobile computing device to broadcast a query or advertisement for trackers nearby; upon receipt of this query or advertisement, the tracker can return a response to the mobile computing device, including an identifier of the tracker. The native application can then: implement computer vision techniques to extract an identifier of the supplement package from the photographic image; retrieve a supplement profile associated with the identifier; add the supplement profile to the user account; and associate a tracker identifier recently received at a greatest signal strength with the supplement profile. The native application can thus link the tracker to the supplement profile in real-time when the user scans a corresponding supplement package to add the supplement profile to the user's account.

In this variation, the native application can also tentatively link the tracker identifier to the supplement profile according to the foregoing process; once this tentative link is established and while the user is still scanning the supplement package with a camera in the mobile computing device, the native application can: transmit a prompt to the tracker to activate an outwardly facing light element; implement computer vision techniques to scan a camera feed for activation of a light element in the field of view of the camera; confirm the link between the tracker identifier and the supplement profile if activation of the light element is detected; and otherwise discard this link and prompt the user to restart the process of pairing the tracker to supplement profile.

However, the native application can interface with the tracker and the user in any other way to automatically load a supplement profile into the user's account and to link this supplement profile to a tracker.

1.6 Regimen

In one variation, upon insertion of a supplement profile into the user's account, the native application writes a regimen for consuming the supplement to the supplement profile. In one implementation, the native application automatically loads a default recommended regimen for the supplement from a supplement manufacturer into the supplement profile; the native application can then interface with the user to modify this default recommended regimen, such as to define specific times or time windows for a default number of recommended daily consumption events for the supplement or to adjust a number of daily consumption events for the supplement.

In another implementation, the native application can: access a portal into an online social network; enable the user to navigate to a profile of a friend, family member, or other connection and to select a regimen for the same supplement from this other profile; copy the regimen from this other profile into the supplement profile in the user's account; and then enable the user to manually adjust parameters of this supplement profile, such as target times, time windows, days of the week, and dose size for consumption events specified in the regimen.

In yet another implementation, the native application can automatically extract a regimen from and/or automatically adjust an existing regimen for the supplement based on historical trends in consumption of the supplement by the user, such as by extracting days, times, and/or locations, etc. that the user consumes the supplement from consumption event data stored in or otherwise associated with the user's account.

1.7 Motion Models

Block S130 of the first method S100 recites retrieving a motion model, from a set of motion models for characterizing a consumption event at the packaging format; and Block S140 of the first method S100 recites uploading the motion model to the tracker. Generally, in Blocks S130 and S140, the native application accesses a motion model best representative of the packaging format of the supplement package and the supplement format of the supplement linked to the tracker in the user account and loads this motion model onto the tracker for subsequent local detection of consumption events at the tracker.

In one implementation shown in FIG. 1, a motion model includes an artificial neural network (e.g., a recurrent artificial neural network with Gated Recurrent Units (GRU) or Long Short Term Memory (LSTM) layers) defining a set of connections, neurons, and layers through which sensor data collected by the tracker is passed to output a determination that a consumption event occurred. For example, the tracker can: regularly sample an accelerometer, gyroscope, tilt sensor, touch or proximity sensor, and ambient light sensor, such as at a rate of 10 Hz while in an active state, as described above; store these sensor data in a buffer (e.g., a rolling or circular buffer) in local memory; and regularly pass these sensor data into the motion model to calculate a confidence score that a consumption event has recently occurred.

A set of (e.g., ten, twenty) motion models can be stored on a remote database, wherein each motion model is associated with a unique combination of package format, supplement format, and/or tracker placement. For example, the remote database can store a first motion model associated with large (e.g., one-liter to five-liter) containers containing supplement in powdered format and with placement of a tracker on a threaded lid. The first motion model can thus output a high confidence score for a consumption event when rotation about a first axis (e.g., unscrewing the lid) followed by translation and rotation about an arc (e.g., tilting and lifting the lid off of the container) are detected by sensors in a tracker coupled to such a lid. In this example, the remote database can also store a second motion model associated with small jars with threaded lids and containing supplements in capsule form and with placement of a tracker on a side of the jar near the neck of the jar. The second motion model can thus output a high confidence score for a consumption event when translation about a first axis (e.g., lifting from a table) followed by jerky rotation about the first axis (e.g., removing the threaded lid) and then rotation about a second axis perpendicular to the first axis (e.g., tilting to dispense a capsule from the jar) are detected by sensors in a tracker coupled to such a jar. In this example, the remote database can also store a third motion model associated with a small bottle with dropper containing liquid supplement and with a tracker coupled to a side of the bottle. The third motion model can thus output a high confidence score for a consumption event when translation about a first axis (e.g., lifting from a table) followed by jerky rotation about the first axis (e.g., removing the threaded dropper) and then jerky motion along the first axis (e.g., inserting and removing the dropper) are detected by sensors in a tracker coupled to such a bottle. Furthermore, the remote database can store a fourth motion model associated with small- to medium-sized jars with pop lids and containing supplements in capsule form and with a tracker coupled to a side of the jar. The fourth motion mode can thus output a high confidence score for a consumption event when translation about a first axis (e.g., lifting from a table) followed by sharp acceleration along the first axis (e.g., popping the lid) and then rotation about a second axis perpendicular to the first axis (e.g., tilting to dispense a pill) are detected by sensors in a tracker coupled to such a jar. However, the remote database can store any other number of motion models of any other type and associated with any other combination of package format, supplement format, and/or tracker placement.

Once the tracker is coupled to a supplement package and linked to an instance of a corresponding supplement profile, as described above, the native application can thus download a motion model most representative of the supplement package and the supplement format from the remote database in Block S130 and then transmit the motion model—over wireless communication protocol—to the tracker in Block S140.

1.8 Initial True Positive Consumption Event

In one variation, the native application: prompts the user to consume a dose of the supplement from the supplement package; collects motion (and other) data recorded by the tracker during this consumption event; labels these data as a positive consumption event; and retrains a local or global copy of the motion model on these labeled motion data, thereby tailoring the motion model to detect consumption events between the user and the supplement package and better accommodating for a unique mode in which the user may manipulate the supplement package during a consumption event.

In one implementation, once the native application retrieves the motion model, the native application uploads the motion model to the tracker, serves a command to the tracker to arm the tracker to detect a consumption event, and renders a prompt or notification on the display of the mobile computing device to consume a dose of the supplement from the supplement package. As the user then performs a consumption event according to this prompt, the tracker records motion data (and ambient light data, touch or proximity data, etc.) to local memory, passes these motion data into its local copy of the motion model, and returns a timestamp of the consumption event and these motion data once the motion model outputs a confidence score for a consumption event above a low initial threshold (e.g., 50%). Upon receipt of these data, the native application (and/or a remote computer system) can label these motion data with a positive consumption event label, add these motion data to a general training set of historical labeled motion data for similar package and supplement format combinations, retrain the motion model on this extended training set, such as with greater weight applied to the motion data collected from the tracker, and then upload this refined motion model to the tracker. The native application can additionally or alternatively return these labeled motion data to a remote computer system, and the remote computing device can add these labeled motion data to a global training set for this package and supplement format combination, retrain the corresponding motion model on this extended global training set, and distribute this refined motion model to other trackers installed on supplement packages representing a similar package and supplement format combination.

However, the native application can interface with the tracker and/or the remote computer system to retrain a motion model uniquely for the tracker or generally for a population of trackers based on motion data collected by the tracker during initial setup of the tracker on a supplement package.

1.9 Regular Consumption Event Detection

Block S150 of the first method S100 recites characterizing motion of the supplement package as a consumption event based on the motion model; and Block S152 of the first method S100 recites transmitting a time of the consumption event to the mobile computing device. Generally, in Blocks S150 and S152, the tracker implements the motion model to transform data read from its integrated sensors into a determination of whether a consumption event occurred at the tracker, such as in the form of a confidence score, based on its local copy of the motion model and returns a signal indicating detection of a consumption event by the tracker—such as a timestamp of the consumption event and an identifier of the tracker, which is linked to the supplement profile in the user account—to the mobile computing device when this confidence score exceeds a preset threshold value (e.g., 80%), as shown in FIG. 1.

In one implementation, the tracker defaults to a sleep state in which the wireless communication module and various controller functions are disabled in order to limit power consumption. However, the controller can transition to an active state when outputs of the motion sensor (e.g., accelerometer), the touch or proximity sensor, and/or the ambient light sensor change or exceed preset thresholds, thereby indicating that the tracker is being handled by a user. Once in the active state, the controller can regularly: sample the motion sensor, the touch or proximity sensor, and/or the ambient light sensor, such as at a rate of 10 Hz; and pass these data into its local copy of the motion model to calculate a confidence score for a consumption event in Block S150. If the confidence score exceeds a preset threshold value, the tracker can then: activate a light element in the tracker to indicate that a consumption event was detected, such as by flashing an LED in the tracker three times; wirelessly broadcast a query to connect to the mobile computing device; and send a timestamp of the consumption event and the identifier of the tracker to the mobile computing device if a wireless connection is established within ten seconds of transmitting the initial inquiry.

However, if the tracker fails to establish a connection to the mobile computing device, the tracker can store the timestamp of the computer system and related metadata in a local buffer until a next consumption event is detected. When the confidence score calculated for a next consumption event exceeds the preset threshold, the tracker can: again broadcast a query to connect to the mobile computing device; send a timestamp of this new consumption event and timestamps of consumption events stored in the local buffer to the mobile computing device; and then clear the buffer. However, if the tracker again fails to establish a wireless connection with the mobile computing device, the tracker can repeat this process until connection to the mobile computing device is established following detection of a consumption event in the future.

As described above, the tracker can also: store motion (and other data) that triggered detection of a consumption event in local memory; and upload these motion data to the mobile computing device for further handling by the native application, such as to retrain the motion model. For example, if the confidence score for a consumption event falls within an ambiguous score range (e.g., 60%-80%), the tracker can upload related motion data and an ambiguous consumption event flag to the mobile computing device. Upon receipt of these data and the flag, the native application can render a prompt on the display of the mobile computing device to confirm or refute the consumption event. The native application can then label these motion with the user's feedback responsive to this prompt and retrain the motion model accordingly, thereby developing the motion model to detect consumption events uniquely performed by the user for the packaging and supplement format combination.

1.10 Consumption Event Confirmation

In one variation, upon receipt of detection of a consumption event from the tracker (e.g., including a timestamp and confidence score of the consumption event), the native application can confirm or discard the consumption event based on additional data, such as based on alignment between the consumption event and historical trends in consumption of the supplement by the user and/or based on alignment between the consumption event and a regimen associated with the supplement in the user's account.

1.10.1 Trends

In one implementation, the native application: writes consumption events to a log in the user's account; and implements regression techniques to extract a consumption trend for the supplement from historical consumption events stored in this log, such as for the current supplement package only or for all consumption events involving the same supplement type consumed by the user over time (e.g., from multiple like supplement packages). For example, the native application can extract trends in consumption events in discrete intervals, such as: per day; per weekday; per morning, afternoon, evening, and nighttime time window; per specific day of the week; etc. Once the native application extracts a consumption trend from these consumption event data, the native application can: calculate a deviation in the time and date of a new consumption event from this trend; refine the confidence score for the new consumption event inversely proportional to this deviation; confirm and write the consumption event for the supplement to the log if the refined consumption score still exceeds a preset threshold; and otherwise discard the consumption event or label the consumption event as anomalous.

In another implementation, the native application can: implement k-means clustering techniques to cluster times of historical consumption events for the supplement by the user; implement k-nearest neighbor techniques to calculate a distance from the time and date of the new consumption event to these clusters of historical consumption events; refine the confidence score for the new consumption event inversely proportional to this distance; confirm and write the new consumption event for the supplement to the log if the refined consumption score still exceeds the threshold; and otherwise discard the consumption event or label the consumption event as anomalous.

1.10.2 Regimen Deviation

In another implementation, if the tracker detects a new consumption event (e.g., calculates a consumption event confidence score that exceeds a threshold score) at a time that differs significantly from a scheduled consumption time specified by the corresponding regimen, the native application can flag the new consumption event as anomalous. Conversely, the native application can confirm the new consumption event if the time of the new consumption event aligns with (i.e., falls within or matches) a scheduled time window or target time for consumption of the supplement, as defined in the corresponding regimen.

For example, upon receipt of a consumption event from the tracker, the native application can: calculate a distance (i.e., a time offset) from the timestamp of the consumption event to a nearest target day and time for consumption of the supplement, as specified in the regimen; refine the confidence score for the consumption event inversely proportional to this distance; confirm and log the consumption event for the supplement in the user's account if the refined confidence score still exceeds the threshold; and otherwise discard the consumption event or label the consumption event as anomalous.

1.10.3 Mobile Computing Device Proximity

In yet another implementation, the tracker or the native application can confirm the new consumption event based on proximity of the tracker to the mobile computing device during or immediately after the consumption event. In particular, the user is likely to be near her mobile computing device (e.g., carried in her pocket, placed on her desk nearby) throughout the day; a new consumption event may therefore be likely to occur in the presence of the user's mobile computing device; and the tracker or the native application can confirm a new consumption event if a wireless connection between the tracker and the mobile computing device is established soon after the tracker detects a consumption event and queries the mobile computing device for a wireless connection.

In one example, in response to calculating a confidence score for a new consumption event that exceeds the preset threshold score, the tracker: broadcasts a query requesting connection to the mobile computing device; increases the confidence score for the consumption event if a response is received from the mobile computing device soon thereafter, thus indicating proximity of the mobile computing device to the tracker at the time of the new consumption event; and then uploads a timestamp of the new consumption event to the mobile computing device accordingly. Alternatively, the tracker or the native application can tag the consumption event as occurring in the vicinity of the mobile computing device; and the native application can then interpret this tag as a higher probability or confirmation that the new consumption event is a true positive consumption event.

1.10.4 Manual Confirmation and Motion Model Retraining

As described above, the native application can flag a new consumption event if a confidence score received from the tracker or if a confidence score adjusted based on trends, corresponding regimen, or proximity to the mobile computing device falls below the threshold score or within an ambiguous score range (e.g., 60%-80%). The native application can then: label the consumption event as ambiguous; serve a prompt to the user to confirm whether the consumption event occurred at the time recorded by the tracker; and write the consumption event to the log in the user's account given a positive response from the user. In this implementation, the native application can also: retrieve motion data for this consumption event from the tracker (e.g., stored in a buffer on the tracker), as described above; label these motion data based on a user's response to the prompt; add these labeled data to a user-specific or global training set for the motion model; retrain the motion model on this extended training set; and send this updated motion model to tracker.

1.10.5 Consumption Location

In one variation, upon receipt of consumption event data from the tracker, the native application can: compare the timestamp of the consumption event to the current time to confirm that the detected consumption event was recent (e.g., within the last thirty seconds); implement the foregoing methods and techniques to confirm the consumption event, such as automatically or under guidance from the user; sample a geolocation sensor or query an operating system on the mobile computing device for the geolocation of the mobile computing device; and record the consumption event data received from the tracker and the geolocation of the mobile computing device at approximately the time of the consumption event to a log in the user's account. The native application can then generate a map (e.g., a geographic "heatmap") representing locations at which the user consumes the supplement over time.

1.11 Motion Model Correction

In one variation, the native application updates the motion model loaded onto the tracker based on a quantity of supplement remaining in the supplement package. In particular, a user may manipulate a supplement package differently during a consumption event when the supplement package is full, when the supplement package is half full, and when the supplement package is nearly empty. To compensate for this change, the native application can upload a revised or different motion model to the tracker to enable the tracker to accurately and repeatably detect consumption events as the supplement package is emptied over time.

In one implementation, the native application: retrieves an original weight of supplement, volume of supplement, or number of supplement pills, etc. contained in the full supplement package, such as from the supplement profile once loaded in the user account; retrieves a standard dose size for the supplement from the supplement profile; and calculates a number of standard-sized doses in the supplement package accordingly. Alternatively, the native application can retrieve a total number of standard-sized doses in the supplement package directly from the supplement profile. Over time, the native application can then sum a number of consumption events associated with the supplement since the current supplement package was linked to the tracker and subtract this sum from the total number of standard-sized doses in the supplement package to determine a current fill level of the supplement package.

Thus, as the fill level of the supplement package decreases to outside of a fill level range supported by a motion model currently loaded on the tracker (e.g., a fill level range for which the accuracy of the motion model for detecting true positive consumption events with minimal false negative and false positive outputs), the native application can retrieve an alternate motion model for the same supplement and package format combination but different fill level range from the remote database and then upload this alternate motion model to the tracker. The native application can repeat this process over time as the supplement package is emptied.

Furthermore, the native application can receive an indication from the user when the supplement package is empty, such as in the form of direct confirmation that the supplement package is empty or through initiation of a paring routine to link the same or other tracker to another supplement package containing the same supplement. The native application can then divide the total number of standard-sized doses in the supplement package by the total number of consumption events recorded at the supplement package to calculate an actual dose size for the supplement by the user. The native application can then implement this actual dose size to estimate fill level of supplement packages containing the same supplement and linked to the user's account in the future.

1.12 Multiple Trackers and Supplements

As shown in FIG. 3, the native application can implement the foregoing methods and techniques to interface with multiple or many (e.g., two, ten, fifty) trackers arranged across a group of supplement packages containing multiple unique supplements associated with supplement profiles loaded into the user's account in order to monitor and guide the user's consumption of these supplements over time.

2. Second Method

Figure 4:
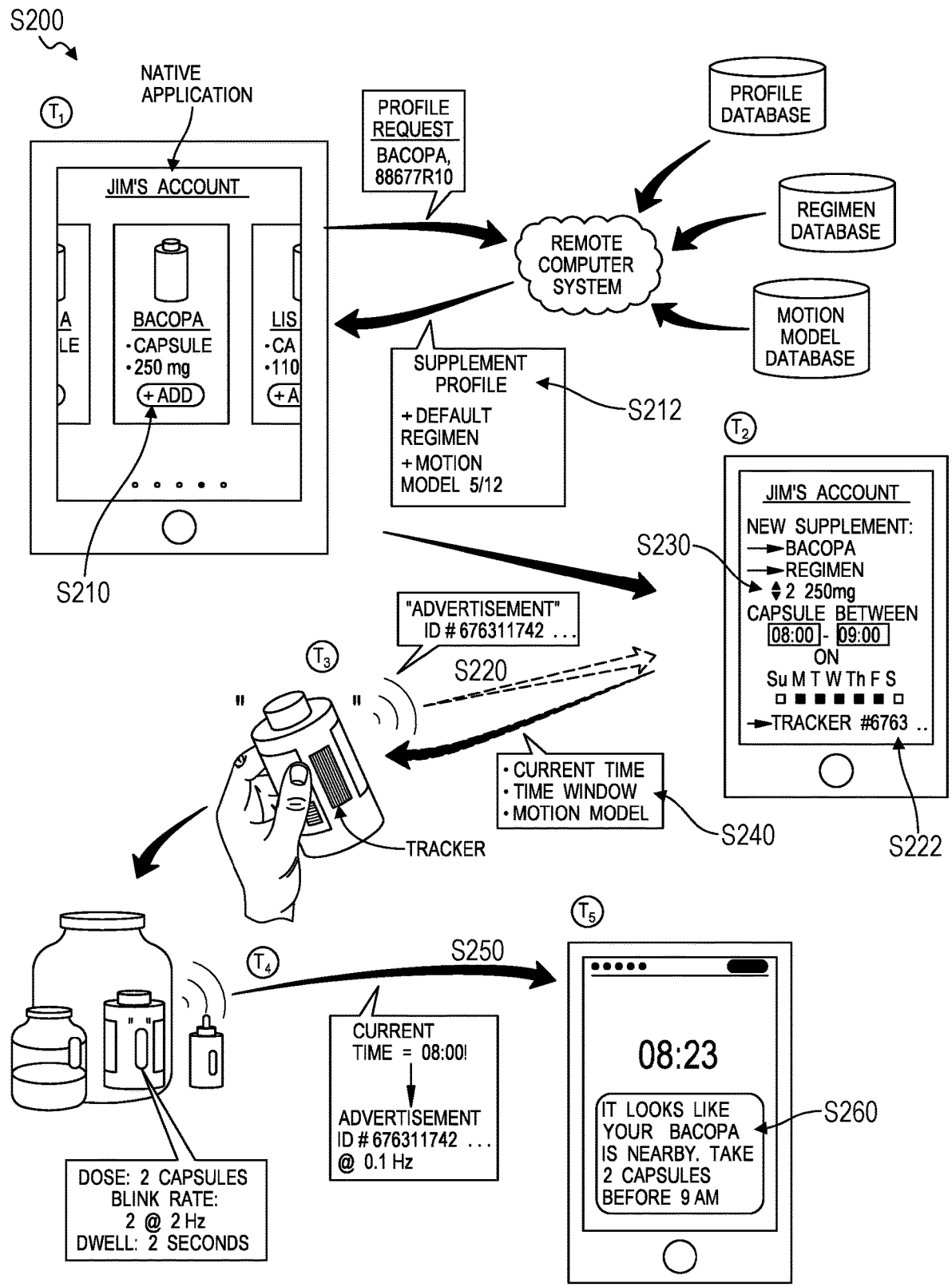
FIG. 4 is a flowchart representation of a second method.

As shown in FIG. 4, a second method S200 for guiding consumption of supplements by a user includes, at a software program executing on a mobile computing device: receiving a selection of a supplement, from a set of known supplements, contained in a supplement package of a particular packaging format in Block S210; loading a supplement profile of the supplement into a user account in Block S212; receiving an identifier broadcast wirelessly by a tracker placed on the supplement package in Block S220; linking the identifier to the supplement profile in the user account in Block S222; associating a regimen with the supplement profile in the user account in Block S230, the regimen specifying a time window for consumption of a dose of the supplement from the supplement package; and loading the time window from the regimen onto the tracker in Block S240. The second method S200 also includes: at the tracker, in response to a current time falling within the time window, broadcasting a wireless advertisement over a limited distance range in Block S250; and, at the software program, in response to receiving the wireless advertisement from the tracker, rendering a notification to consume a dose of the supplement on a display of the mobile computing device in Block S260.

2.1 Applications

The second method S200 can be executed by a system including a wireless tracker and a software program (hereinafter a "native application") executing on a mobile computing device to opportunistically serve reminders to a user to consume a supplement when the user's mobile computing device—and, by proxy, the user—is near this supplement at a predefined consumption time for this supplement. In particular, the native application: hosts a user account on a user's mobile computing device (e.g., smartphone, tablet, smartwatch) (or to a local fixed device, such as a hub or wall wart); enables the user to add and remove supplements from her user account; enables the user to set and adjust a regimen for consumption of these supplements; interfaces with a set of like trackers arranged on supplement packages containing supplements to track consumption of supplement doses by the user from these supplement packages over time; monitors the user's proximity to these supplement packages based on wireless communications between the mobile computing device and trackers installed on these supplement packages; and selectively serves notifications to the user to consume these supplements when specific conditions are met, such as when the user is near a particular supplement package at a time that falls within a time window for consumption of this supplement, as specified in a regimen for this supplement stored in the user's account. Therefore, the native application can serve a reminder to the user to consume a supplement only when such a notification is particularly relevant to the user.

The native application can also load time windows for consumption of a supplement onto a tracker installed on a supplement package containing this supplement, and the tracker can selectively broadcast wireless advertisements when this time window is current. The native application can thus determine that the tracker is near the mobile computing device upon receipt of such an advertisement from the tracker and issue a reminder accordingly; the tracker can then return to a lower-power state in order to extend battery life once the native application confirms receipt of the advertisement, once the current time falls outside of the time window, or once the tracker detects a consumption event at the supplement package. The tracker can also locally output a visual, auditory, and/or haptic reminder to consume the supplement when the current time falls within the time window if a consumption event has not yet been detected by the tracker within the time window, thereby reminding the user to consume the supplement if the user does not currently have access to her mobile computing device.

However, the native application can interface with a tracker of any other type, of any other form, and configured to transiently mount to a supplement package or intransiently integrated into a supplement package. Furthermore, while described in the context of supplements, the second method S200, native application, and tracker can be implemented in conjunction with a prescription medication, over-the-counter medication, food or a diet regimen, or any other product related to health or wellness.

2.2 Tracker Pairing

Block S220 of the second method S200 recites receiving an identifier broadcast wirelessly by a tracker placed on the supplement package; and Block S222 of the second method S200 recites linking the identifier to the supplement profile in the user account. Generally, in Blocks S220 and S222, the native application can record a physical pairing between the tracker and the supplement package in the corresponding supplement profile in the user account, thereby enabling the native application to subsequently track consumption of the supplement and monitor the user's adherence to a corresponding regimen based on receipt of consumption event data from the tracker over time, as shown in FIG. 4.

In one implementation, once a supplement profile is added to the user's account, the user can confirm whether consumption of supplements from the supplement package is to be monitored with a tracker. For example, the user can manually toggle a virtual switch in the supplement profile or adjacent an image of the supplement or supplement package in a virtual shelf in the user's account rendered in the native application. If the user indicates that the consumption of the supplement is to be monitored with a tracker coupled to the supplement package, the native application can interface with the tracker to execute a paring routine to link a tracker to the user account and to confirm a physical connection between the tracker and the supplement package.

2.2.1 Tracker Detection

The user may install a tracker on a supplement package by applying a disposable element of the two-part hook-and-loop attachment system onto the supplement package and then depressing a non-disposable element of the two-part hook-and-loop attachment system over this disposable element to transiently mount the tracker to the supplement package.

The user can then tap, double-tap, shake, or otherwise manipulate the tracker to prompt the tracker to pair with the mobile computing device. The tracker can monitor its motion through its integrated motion sensors and then broadcast a query—including an identifier of the tracker (e.g., a universally unique identifier, or "UUID") and a request to connect to a local computing device—if its motion (e.g., acceleration) exceeds a predefined threshold. Upon receipt of this query from the tracker in Block S220, the native application can: establish a wireless connection to the tracker; and link the identifier of the tracker to the supplement profile in the user's account in Block S222. For example, the user can tap the mobile computing device against the tracker; this impact can trigger the tracker to broadcast a query to connect to a computing device nearby; the native application can also register this impact through motion sensors in the mobile computing device and record this connection between the identifier of the tracker and the supplement profile in Block S222 based on receipt of this query from the tracker just after registering this impact. In this example, the native application can also confirm this impact between the mobile computing device and the tracker and thus confirm the connection between the identifier of the tracker and the supplement profile based on a high signal strength of the query received from the tracker (i.e., due to proximity between the tracker and the mobile computing device at the time of the impact).

In another implementation, the tracker wakes into an active mode automatically when outputs of various sensors in the tracker indicate that the tracker is being placed on a supplement package. For example, the tracker can wake and broadcast a query, as described above, when a set of environmental conditions are met, including: a change in output of the touch or proximity sensor (e.g., a capacitance sensor) indicating presence of a body (e.g., a hand) on or near the tracker; a drop in ambient light level detected by the ambient light sensor indicating that the ambient light sensor is obscured by a hand or finger; and acceleration followed by deceleration of the tracker indicates that the tracker is being placed on a supplement package. Upon receipt of the query—including the tracker identifier—from the tracker, the native application can link the tracker identifier to the supplement profile in the user's account, as described above.

In the foregoing implementation, the tracker can be configured to execute this process during first use (i.e., "out of the box"). However, if the tracker has been previously used on another supplement package, the native application can predict that the particular tracker—such as in a set of trackers maintained by the user—will be moved to another supplement package if a supplement package previously linked to the tracker is determined to be empty or if the user removes a supplement profile previously linked to the tracker from her user account; the native application can then broadcast a command to the tracker to prepare for detection of transfer to another supplement package.

However, the tracker can initiate a wireless connection with the mobile computing device in any other way and in response to any other event in Block S220 to prompt the native application to link the tracker to a supplement profile—representative of the physical supplement package physically paired with the tracker—in the user's account in Block S222.

2.2.2 Automatic Loading of Supplement Profile into User Account

In one variation, the user: initiates a pairing routine at the native application, such as by adding a new supplement profile to her user account, as described above; removes a new tracker from its packaging or removes a used tracker from an empty, expired, or discarded supplement package; places the tracker on a supplement package, such as near a barcode (or other visual identifier); holds the supplement package—with tracker attached—in one hand while capturing a photographic image of the barcode with the mobile computing device held in her other hand. Upon receipt of this photographic image, the native application triggers the mobile computing device to broadcast a query or advertisement for trackers nearby; upon receipt of this query or advertisement, the tracker can return a response to the mobile computing device, including an identifier of the tracker. The native application can then: implement computer vision techniques to extract an identifier of the supplement package from the photographic image; retrieve a supplement profile associated with the identifier; add the supplement profile to the user account; and associate a tracker identifier recently received at a greatest signal strength with the supplement profile in Blocks S220 and S222. The native application can thus link the tracker to the supplement profile in real-time when the user scans a corresponding supplement package to add the supplement profile to the user's account in Blocks S220 and S222.

In this variation, the native application can also tentatively link the tracker identifier to the supplement profile according to the foregoing process; once this tentative link is established and while the user is still scanning the supplement package with a camera in the mobile computing device, the native application can: transmit a prompt to the tracker to activate an outwardly facing light element; implement computer vision techniques to scan a camera feed for activation of a light element in the field of view of the camera; confirm the link between the tracker identifier and the supplement profile if activation of the light element is detected; and otherwise discard this link and prompt the user to restart the process of pairing the tracker to the supplement profile.

However, the native application can interface with the tracker and the user in any other way to automatically load a supplement profile into the user's account and to link this supplement profile to a tracker in Blocks S220 and S222.

2.3 Regimen

Block S230 of the second method S200 recites associating a regimen with the supplement profile in the user account, wherein the regimen specifies a time window for consumption of a dose of the supplement from the supplement package. Generally, upon insertion of a supplement profile into the user's account, the native application can write a regimen for consuming the supplement to the supplement profile.

In one implementation, the native application automatically loads a default recommended regimen for the supplement from a supplement manufacturer into the supplement profile; the native application can then interface with the user to modify this default recommended regimen, such as to define specific times or time windows for a default number of recommended daily consumption events for the supplement or to adjust a number of daily consumption events for the supplement, as shown in FIG. 4. For example, the default regimen can specify consumption of the supplement twice per day, including once between the hours of 7 AM and 8 AM and again between the hours of 7 PM and 8 PM; the native application can then interface with the user to adjust the time windows to 6 AM to 7 AM and from 4 PM to 6 PM.

In another implementation, the native application can: access a portal into an online social network; enable the user to navigate to a profile of a friend, family member, or other connection and to select a regimen for the same supplement from this other profile; copy the regimen from this other profile into the supplement profile in the user's account; and then enable the user to manually adjust parameters of this supplement profile, such as target times, time windows, days of the week, and dose size for consumption events specified in the regimen.

Similalry, another user within the social network may send (e.g., "push") supplement data from her user account to the user's account, such as in the form of a name of the supplement, a SKU or other identifier of the supplement, a supplement profile of the supplement, and/or her regimen for consuming the supplement. Upon receipt of these supplement data from the other user at the user's account, the user can: reject the supplement; accept the supplement and regiment to load the regiment directly into her virtual shelf (described below) and then manually enter changes to the regimen; or open the supplement profile to view more information regarding the supplement before accepting or rejecting the supplement.

In yet another implementation, the native application can automatically extract a regimen from and/or automatically adjust an existing regimen for the supplement based on historical trends in consumption of the supplement by the user, such as by extracting days, times, and/or locations, etc. that the user consumes the supplement from consumption event data associated with the user's account.

However, the native application can implement any other method or technique to define, import, and/or customize a regimen for consumption of a supplement by the user and to link this regimen to a supplement profile in the user's account in Block S230.

(Alternatively, the user can elect no regulated regimen for the supplement, such as by selecting an "as I please" option within the supplement profile.)

Once the regimen is defined and stored in the supplement profile, the native application can upload supplement consumption parameters to the tracker—linked to the supplement profile in the user's account—in Block S240. For example, the native application can transmit a current time and time windows (or specific target times) for consumption of a dose of the supplement to the tracker; upon receipt of these data, the tracker can synchronize its internal clock to the current time and set alarms to trigger transmission of wireless advertisements during these time windows (or around these target times).

2.4 Motion Models

In one variation, the native application also accesses a motion model best representative of the packaging format of the supplement package and the supplement format of the supplement thus linked to the tracker in the user account and loads this motion model onto the tracker for subsequent local detection of consumption events at the tracker, as shown in FIG. 4.

In one implementation, a motion model includes an artificial neural network (e.g., a recurrent artificial neural network with Gated Recurrent Units (GRU) or Long Short Term Memory (LSTM) layers) defining a set of connections, neurons, and layers through which sensor data collected by the tracker is passed to output a determination that a consumption event occurred. For example, the tracker can: regularly sample an accelerometer, gyroscope, tilt sensor, touch or proximity sensor, and ambient light sensor, such as at a rate of 10 Hz while in an active state, as described above; store these sensor data in a buffer (e.g., a rolling or circular buffer) in local memory; and regularly pass these sensor data into the motion model to calculate a confidence score that a consumption event has recently occurred.

Therefore, once the tracker is coupled to a supplement package and linked to an instance of a corresponding supplement profile in Block S222, the native application can download a motion model most representative of the supplement package and the supplement format from a remote database and then transmit the motion model—over wireless communication protocol—to the tracker. During operation, the tracker can: implement the motion model to transform data read from its integrated sensors into a determination of whether a consumption event occurred at the tracker, such as in the form of a confidence score, based on its local copy of the motion model; and return a signal indicating detection of a consumption event by the tracker—such as a timestamp of the consumption event and a identifier of the tracker, which is linked to the supplement profile in the user account—to the mobile computing device when this confidence score exceeds a preset threshold value (e.g., 80%).

In one implementation, the tracker defaults to a sleep state in which the wireless communication module and various controller functions are disabled in order to limit power consumption. However, the controller can transition to an active state when outputs of the motion sensor (e.g., accelerometer), the touch or proximity sensor, and/or the ambient light sensor change or exceed present thresholds, thereby indicating that the tracker is being handled by a user. Once in the active state, the controller can regularly: sample the motion sensor, the touch or proximity sensor, and/or the ambient light sensor, such as at a rate of 10 Hz; and pass these data into its local copy of the motion model to calculate a confidence score for a consumption event. If the confidence score exceeds a preset threshold value, the tracker can then: activate a light element in the tracker to indicate that a consumption event was detected, such as by flashing an LED in the tracker three times; wirelessly broadcast a query to connect to the mobile computing device; and send a timestamp of the consumption event and the identifier of the tracker to the mobile computing device if a wireless connection is established within ten seconds of transmitting the initial inquiry.

2.5 Native Application Reminders

Block S250 of the second method S200 recites, at the tracker, broadcasting a wireless advertisement over a limited distance range in response to a current time falling within the time window; and Block S260 of the second method S200 recites, at the software program, rendering a notification to consume a dose of the supplement on a display of the mobile computing device in response to receiving the wireless advertisement from the tracker. Generally, in Block S250, the tracker can broadcast a short-range (e.g., five-meter) advertisement to indicate its approximate location once the current time falls inside a time window specified for consumption of the supplement according to the regimen; and the native application serves a notification or other prompt to consume a dose of the supplement if such an advertisement is received from the tracker, thereby indicating the mobile computing device—and therefore likely the user—is near the supplement package that contains this supplement.

In one implementation, once the regimen is defined and associated with the supplement profile in Block S230, the native application transmits parameters of the regimen to the tracker currently associated with the supplement profile in the user's account in Block S240, as described above and shown in FIG. 4. As a time window for scheduled consumption of the supplement is current (or as a scheduled time for consumption approaches), the tracker can transition from a sleep state to a low-power broadcast state in which the tracker broadcasts a wireless advertisement (e.g., a "beacon" containing the tracker's identifier) to indicate to devices nearby that the tracker is present. For example, the tracker can broadcast wireless advertisements at a static advertising rate, such as once per five-second interval. Alternatively, the tracker can broadcast advertisements at a dynamic rate, such as: at a rate that increases from once per thirty-second interface at the beginning of the time window to once per five-second interval at the end of the time window; or at a rate that is an inverse function of distance (i.e., time) to a singular scheduled time for consumption of the supplement. The tracker can then cease broadcast of the advertisement and return to a sleep state in order to reduce power consumption and extend battery life: once the current time falls outside of the time window (or different from the scheduled time by more than a threshold duration, such as thirty-minutes); once the tracker detects a consumption event; or once the tracker receives confirmation from the native application that a reminder has already been issued for the supplement, In this implementation, the tracker can broadcast a low-power signal containing the advertisement and of sufficient power to be detected by a mobile computing device at limited distance from the tracker, such as two meters or five meters, as shown in FIG. 4. Upon receipt of such an advertisement from the tracker, the mobile computing device can extract the tracker's identifier from the advertisement, associate the identifier with the native application, and pass the identifier to the native application. The native application can then: query the user's account for identification of the supplement package linked to the tracker's identifier; confirm that the mobile computing device is within this limited distance from the tracker; (access a consumption log to confirm that the user has not already consumed a dose of the supplement within a consumption window specified by the regimen) confirm that the native application has not already issued a notification to consume a dose of this supplement for the current time window; and then serve a reminder to consume a dose of the supplement on the mobile computing device, such as in the form of a badge rendered on a lock screen or in the form of a popup notification on the display of the mobile computing device. For example, the native application can populate the reminder with various information extracted from the supplement profile, such as: a name of the supplement; an image (e.g., a stock image) of the supplement or supplement package; a description of the supplement; a number of doses of the supplement scheduled for the current time window; and/or a difference between the current time and a scheduled time for consumption of the supplement; etc.

Specifically, presence of the mobile computing device near the tracker suggests that the user is near the supplement package; therefore this notification to consume a dose of the supplement—as scheduled in the corresponding regimen—may be immediately actionable by the user when provided to the user immediately after an advertisement is received from the tracker. However, if the tracker is not detected near the mobile computing device—and therefore if presence of the user near the supplement package is not definitive—during the scheduled time window for consumption of the supplement, the native application can withhold such a notification, even if the user is scheduled to consume the supplement at or around the current time since this notification may be unlikely to be immediately actionable by the user.

2.6 Tracker Reminders

In one variation, in addition to serving a local reminder to consume a dose of the supplement on the mobile computing device, the native application can also send a communication to the tracker to activate a light element in the tracker in order to visually communicate to the user that a consumption event is scheduled—according to the regimen—for the supplement contained in the supplement package on which the tracker is installed. In particular, rather than automatically activating the light element in the tracker when a time window for the supplement in the adjacent software program package is current, the tracker can limit activation of the light element to when wireless communication between the tracker and the mobile computing device suggests that the user is near (e.g., within viewing distance of) the supplement package (and to when the tracker detects motion when the time window is current, as described below), thereby reducing power consumption of the tracker over time and extending battery life of the tracker.

In one implementation, upon receipt of a wireless advertisement from the tracker, the native application can return a command to activate a light element or merely return an advertisement or other wireless communication to the tracker. Upon receipt of such command or communication from the tracker, the tracker can activate the light element immediately. Alternatively, the tracker can implement this command to activate the light element: only once an output of the capacitance sensor indicates that a conductive body has come near or into contact with the tracker, which may suggest that the user is touching the supplement package; once an output of the ambient light sensor indicates that the environment around the tracker has changed; and/or only once an output of the accelerometer indicates that the tracker is in motion, such as experiencing an acceleration greater than a threshold value, which may suggest that the user is currently holding the supplement package in preparation for a consumption event.

2.6.1 Light Elements

As described above, the tracker can include an inward-facing light element on the inner surface of the housing and configured to illuminate a translucent supplement package when active such that the supplement package "glows." In one implementation, the native application can: access a type of the supplement package from the supplement profile to determine whether the supplement package is translucent and therefore a candidate for inward lighting; and then configure the tracker accordingly during setup or when sending a command back to the tracker to activate the light element during a current time window. The tracker can thus selectively activate the inward-facing light element, such as by intermittently activating the light element at a rate of one second per five second interval. However, if the supplement package is opaque or otherwise not a candidate for inward illumination, the tracker can selectively activate an outward-facing light element and/or a haptic module (e.g., a vibrator) to locally prompt a consumption event at the supplement package.

2.6.2 Haptics

In one variation, the tracker additionally or alternatively includes a haptic module, such as a vibrator. The tracker can thus activate the haptic module to tactilely and/or audibly prompt a consumption event at the supplement package, such as by intermittently pulsing the haptic module when a time window for consumption of the supplement is current and a wireless communication has been received from the mobile computing device to indicate its proximity to the tracker and/or the tracker detects a change in its environment.

However, the tracker can include any other one or more visual, haptic, auditory, and/or other elements or modules configured to prompt a user to consume a dose of a supplement from the corresponding supplement package.

2.6.3 Group Reminders

In one variation, if the tracker and supplement package are grouped with other trackers arranged on other supplement packages, the tracker can selectively activate its light element(s) in different colors to indicate whether the supplement contained in the supplement package is due for consumption or is not due for consumption in order to reduce user confusion when managing multiple supplements at once.

In one example: a first tracker—in a group of trackers—is arranged on a first supplement package containing a first supplement scheduled for consumption around the current time; and a second tracker in the group is arranged on a second supplement package containing a second supplement that is not scheduled for consumption around the current time. As described above, the first tracker broadcasts a wireless advertisement responsive to the time window for the first supplement being current; upon receipt of the wireless advertisement, the native application: confirms proximity of the mobile computing device to the first trackers; determines the geolocation of the mobile computing device; accesses the user's consumption event log to determine that the user has historically consumed the second supplement around this geolocation in the past; and sends a first command to the first tracker to activate the inwardly- (or outwardly) facing light element on the first tracker in a first color (e.g., green) to indicate that the user should consume a dose of supplement from the first supplement package; and sends a second command to the second tracker to activate the inwardly- (or outwardly) facing light element on the second tracker in a second color (e.g., red) to indicate that the user is not scheduled to consume a dose of supplement from the second supplement package.

Alternatively, in the foregoing example, the second tracker can also receive the wireless advertising from the first tracker and then broadcast its own wireless advertisement accordingly; upon receipt of this second wireless advertisement, the native application can identify the second tracker, confirm that the second supplement is not due for consumption, and return a command to the second tracker to activate its light element in the second color.

In a similar example: the first tracker in the group is arranged on a first supplement package for which a consumption event around the current time is specified in a corresponding regimen; the second tracker is arranged on a second supplement package for which a consumption event—per a corresponding regimen—has recently been detected; and the native application receives a wireless advertisement from the first and/or second trackers and thus confirms proximity of the mobile computing device to the trackers. In this example, the native application then: sends a first command to the first tracker to flash the inwardly- (or outwardly) facing light element on the first tracker in a solid green color to indicate that the user should consume a dose of supplement from the first supplement package; and send a second command to the second tracker to activate the inwardly- (or outwardly) facing light element on the second tracker in a solid red color to indicate that the user is not scheduled to consume another dose of supplement from the second supplement package

2.7 Dosage

In one variation, the native application uploads dosage information to the tracker, including a number of dosing units (e.g., pills, drops, scoops, etc.) per consumption event; and the tracker outputs a visual and/or haptic signal to indicate this number of dosing units to the user in addition to outputting a visual and/or haptic signal to locally indicate that a consumption event is currently pending at the supplement package.

In the implementation described above in which the tracker includes a light element, the tracker can regularly pulse the light element when certain conditions are met—such as the mobile computing device is nearby, the current time aligns to a target consumption time for the supplement, and/or the supplement package has been moved or jostled—in order to remind the user to consume a dose from the supplement package while the user is nearby. In this implementation, the tracker can also indicate a quantity of doses of the supplement to consume from the supplement package by altering a flash rate of the light element, as shown in FIG. 4. For example, the tracker can rapidly flash the light element at a rate of 2 Hz and a number of times corresponding to the number of doses per consumption event specified in the regimen associated with the supplement in the user's account. In this example, the tracker can then deactivate the light element over a dwell period (e.g., two seconds) before rapidly flashing the light element the same number of times at the rate of 2 Hz. In this example, for a supplement associated with a regimen specifying two doses, the tracker can thus activate the light element in a "pulse, pulse, pause, pulse, pulse, pause, etc." sequence in order to visually indicate that a consumption event in which two doses are consumed at the supplement package in pending.

For the tracker that includes a haptic module, the tracker can implement similar methods and techniques to pulse the haptic module according to a similar pattern in order to haptically indicate the number of doses of the supplement that the user is scheduled to consume at or around the current time.

2.8 Local Control

As described above, the native application can also upload parameters of a regimen—such as including a target time, time window, days of the week, number of dose units, etc. for each consumption event—to a tracker physically paired with a supplement package containing this supplement. The native application can also synchronize a local timer on the tracker to a global time. The tracker can then implement the foregoing methods and techniques independent of the mobile computing device to automatically output a visual and/or haptic signal when certain conditions are detected, such as: the target time or time window is approaching or current; a change in output of the capacitance sensor indicates that a conductive body has moved near or contacted the supplement package; and/or a change in output of the ambient light sensor indicates that the environment around the supplement package has changed (e.g., that the supplement package has been removed from a drawer, removed from a cupboard, or picked up).

2.9 Tracker Response to Consumption Event

As described above, the tracker can pass motion, ambient light level, and/or capacitance values read from sensors integrated into the tracker into a local copy of a motion model to calculate a confidence score for recent occurrence of a consumption event. The tracker can also: calculate a degree of alignment (or distance) between the current time and a target consumption time or time window assigned to the supplement; and pass a quantitative value representative of this degree of alignment into the motion model to affect the confidence score or otherwise adjust the confidence score for occurrence of a consumption event proportional to this degree of alignment (i.e., inversely proportional to a difference between the current time and the target consumption time or time window assigned to the supplement.) If the confidence score thus calculated by the tracker exceeds a preset threshold score, the tracker can: confirm a consumption event; and broadcast data indicating detection of a consumption event to the mobile computing device, such as including a timestamp of the detected consumption event, the identifier of the tracker, and the confidence score.

Furthermore, once the tracker confirms the consumption event, the tracker can deactivate its internal light elements and/or haptic module to indicate that the user's consumption of the supplement is current. Alternatively, once the tracker confirms the consumption event, the tracker can change an output color of its light element(s), such as by transitioning from blinking a green color to solid a red color for a preset duration (e.g., one minute) to indicate that a consumption event has been detected and to indicate to the user which supplement, in a group of supplements nearby, has recently been consumed. In this implementation, after communicating occurrence of the consumption event to the mobile computing device, the tracker can also interface with the native application, such as described above, to confirm that the mobile computing device is near the tracker. Once the mobile computing device moves away from the tracker, the tracker can deactivate the light element, such as before the expiration of this preset duration in order to reduce power consumption by the tracker following consumption events.

2.10 Multiple Trackers and Supplements

As shown in FIGS. 3 and 4, the native application can implement the foregoing methods and techniques to interface with multiple or many (e.g., two, ten, fifty) trackers arranged across a group of supplement packages containing multiple unique supplements associated with supplement profiles loaded into the user's account in order to monitor and guide the user's consumption of these supplements over time.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for tracking consumption of supplements by a user comprising:
   at a software program executing on a mobile computing device:
      receiving a selection of a supplement contained in a supplement package of a particular packaging format;
      loading a supplement profile of the supplement into a user profile;
      retrieving a motion model, from a set of motion models, for characterizing consumption events at the particular packaging format; and
      uploading the motion model to a tracker; and
   at the tracker:
      characterizing motion of the tracker as a consumption event at the supplement package based on the motion model; and transmitting a time of the consumption event to the mobile computing device.

2. The method of claim 1, further comprising:
during a second time period, calculating a confidence score for a second consumption event at the supplement package based on the motion model and motion of the tracker;
recording a second time of the second consumption event;
in response to the confidence score falling below a threshold score:
flagging the second consumption event; and
serving a prompt to the user to confirm the second consumption event; and
in response to confirmation of the second consumption event by the user:
recording the second consumption event to a consumption event log in the user profile; and
retraining the motion model based on motion of the tracker during the second time period.

3. The method of claim 1, further comprising, at the mobile computing device, rendering an instruction for placement of the tracker on the supplement package based on the particular packaging format.

4. The method of claim 1, further comprising confirming the consumption event based on connectivity between the tracker, coupled to the supplement package, and the mobile computing device.

5. The method of claim 1, further comprising:
associating a regimen with the supplement profile in the user account, the regimen specifying a time window for consumption of a dose of the supplement from the supplement package;
loading the time window from the regimen onto the tracker;
at the tracker, in response to a current time falling within the time window, broadcasting a wireless advertisement over a limited distance range; and
at the mobile computing device, in response to receiving the wireless advertisement from the tracker, rendering a notification to consume a dose of the supplement on a display of the mobile computing device.

6. The method of claim 1:
further comprising
associating a regimen with the supplement profile in the user account, the regimen specifying a time window for consumption of a dose of the supplement from the supplement package;
loading the time window from the regimen onto the tracker; and
at the tracker, in response to a current time falling within the time window, broadcasting a wireless advertisement over a limited distance range; and
wherein characterizing motion of the tracker as the consumption event at the supplement package comprises characterizing motion of the tracker as the consumption event at the supplement package, based on the motion model, responsive to receipt of a response to the wireless advertisement.

7. The method of claim 1, further comprising:
receiving a second selection of a second supplement contained in a second supplement package of a second packaging format;
loading a second supplement profile of the second supplement into the user profile;
retrieving a second motion model, from the set of motion models, for characterizing consumption events at the second packaging format; and at the tracker:
characterizing motion of the tracker as a second consumption event at the second supplement package based on the second motion model; and
transmitting a second time of the consumption event to the mobile computing device.

8. A method for guiding consumption of supplements by a user comprising:
receiving an image of a supplement package, of a particular packaging format, containing a supplement;
detecting a set of features in the image;
identifying the supplement based on the set of features;
retrieving the supplement profile in response to identifying the supplement;
presenting the supplement profile to the user;
receiving confirmation of the supplement profile from the user;
loading a supplement profile of the supplement into a user account;
receiving an identifier broadcast wirelessly by a tracker coupled to the supplement package;
linking the identifier to the supplement profile in the user account based on temporal proximity of receipt of the image and receipt of the identifier from the tracker;
associating a regimen with the supplement profile in the user account, the regimen specifying a time window for consumption of a dose of the supplement from the supplement package; and
at a mobile computing device, in response to receiving a wireless advertisement from the tracker during the time window, generating a prompt to consume a dose of the supplement on a display of the mobile computing device.

9. The method of claim 8, further comprising, at the tracker, in response to a current time falling within the time window, broadcasting the wireless advertisement over a limited distance range.

10. A method for guiding consumption of supplements by a user, the method comprising:
receiving a selection of a supplement contained in a supplement package of a particular packaging format;
loading a supplement profile of the supplement into a user account;
receiving an identifier broadcast wirelessly by a tracker coupled to the supplement package;
linking the identifier to the supplement profile in the user account;
associating a regimen with the supplement profile in the user account, the regimen specifying a time window for consumption of a dose of the supplement from the supplement package;
at a mobile computing device, in response to receiving a wireless advertisement from the tracker during the time window, generating a prompt to consume a dose of the supplement on a display of the mobile computing device;
retrieving a motion model, from a set of motion models, for characterizing consumption events at the particular packaging format;
characterizing motion of the supplement package during the time window as a consumption event at the supplement package based on the motion model; and
recording a time of the consumption event.

11. The method of claim 10:
further comprising loading the motion model onto the tracker; and wherein characterizing motion of the supplement package during the time window as the consumption event comprises, at the tracker:
    capturing a sequence of motion data of the tracker; and
    characterizing motion of the supplement package during the time window as the consumption event at the supplement package based on the sequence of motion data of the tracker and the motion model stored on the tracker.

12. The method of claim 10, further comprising:
during a second time period, calculating a confidence score for a second consumption event at the supplement package based on the motion model and motion of the supplement package;
recording a second time of the second consumption event;
in response to the confidence score falling below a threshold score:
    flagging the second consumption event; and
    serving a prompt to the user to confirm the second consumption event; and
in response to confirmation of the second consumption event by the user:
    recording the second consumption event to a consumption event log in the user profile; and
    retraining the motion model based on motion of the tracker during the second time period.

13. The method of claim 10, further comprising:
at the mobile computing device, rendering an instruction for placement of the tracker on the supplement package based on the particular packaging format; and
loading the motion model onto the tracker.

14. A method for tracking consumption of supplements by a user comprising:
receiving a selection of a supplement contained in a supplement package of a particular packaging format;
loading a supplement profile of the supplement into a user profile;
retrieving a motion model, from a set of motion models, for characterizing consumption events at the particular packaging format; and
based on connectivity between a tracker coupled to the supplement package and a mobile computing device during a first time period:
    characterizing motion of the supplement package as a consumption event at the supplement package based on the motion model; and
    recording a time of the consumption event.

15. The method of claim 14, further comprising:
during a second time period, calculating a confidence score for a second consumption event at the supplement package based on the motion model and motion of the supplement package;
recording a second time of the second consumption event;
in response to the confidence score falling below a threshold score:
    flagging the second consumption event; and
    serving a prompt to the user to confirm the second consumption event; and
in response to confirmation of the second consumption event by the user:
    recording the second consumption event to a consumption event log in the user profile; and
    retraining the motion model based on motion of the supplement package during the second time period.

16. The method of claim 14:
further comprising:
    rendering an instruction for placement of a tracker on the supplement package based on the packaging format; and
    uploading the motion model to the tracker; and
wherein characterizing motion of the supplement package as the consumption event comprises:
    characterizing motion of the tracker as the consumption event at the supplement package based on the motion model and motion of the tracker; and
    confirming the consumption event based on wireless connectivity between the tracker and the mobile computing device.

17. The method of claim 14:
wherein receiving the selection of the supplement comprises:
    receiving an image of the supplement package;
    detecting a set of features in the image;
    identifying the supplement based on the set of features;
    retrieving the supplement profile in response to identifying the supplement;
    presenting the supplement profile to the user; and
    receiving confirmation of the supplement profile from the user; and
further comprising:
    receiving a unique identifier transmitted wirelessly by the tracker; and
    linking the unique identifier to the supplement profile in the user profile.

18. The method of claim 14, further comprising:
receiving a second selection of a second supplement contained in a second supplement package of a second packaging format;
loading a second supplement profile of the second supplement into the user profile;
retrieving a second motion model, from the set of motion models, for characterizing consumption events at the second packaging format;
based on connectivity between a second tracker coupled to the second supplement package and the mobile computing device:
    characterizing motion of the second supplement package as a second consumption event at the second supplement package based on the second motion model; and
    recording a second time of the second consumption event; and
recording the consumption event and the second consumption event in the user profile.

19. The method of claim 14, further comprising:
associating a regimen with the supplement profile in the user account, the regimen specifying a time window for consumption of a dose of the supplement from the supplement package;
loading the time window from the regimen onto the tracker;
at the tracker, in response to a current time falling within the time window, broadcasting a wireless advertisement; and
at the mobile computing device, in response to receiving the wireless advertisement from the tracker, rendering a notification to consume a dose of the supplement on a display of the mobile computing device.

* * * * *